United States Patent [19]

Wilkinson

[11] Patent Number: 5,246,456
[45] Date of Patent: Sep. 21, 1993

[54] FENESTRATED GASTRIC POUCH

[76] Inventor: Lawrence H. Wilkinson, 1516 Columbia Dr. NE., Albuquerque, N. Mex. 87106

[21] Appl. No.: 895,139

[22] Filed: Jun. 8, 1992

[51] Int. Cl.⁵ ............................................. A61F 2/04
[52] U.S. Cl. .................................... 623/12; 623/11
[58] Field of Search .................. 600/37; 623/11, 12, 623/1, 2; 128/898, 899

[56] References Cited

U.S. PATENT DOCUMENTS

| | | | |
|---|---|---|---|
| 3,983,863 | 10/1976 | Janke et al. | 600/37 |
| 4,271,828 | 6/1981 | Angelchik | 600/37 |
| 4,366,581 | 1/1983 | Shah | 623/2 |
| 4,403,604 | 9/1983 | Wilkinson et al. | 600/37 |
| 4,497,074 | 2/1985 | Rey et al. | 623/12 |
| 4,747,849 | 5/1988 | Galtier | 623/12 |
| 4,770,664 | 9/1988 | Gogolewski | 623/12 X |
| 4,854,316 | 8/1989 | Davis | 623/12 X |

OTHER PUBLICATIONS

"Surgery for the Morbidly Obese Patient"; Mervyn Deitel, M. D. Lea & Febiger; 1989; pp. 261–279.

Primary Examiner—Randall L. Green
Assistant Examiner—Gina M. Gualtieri
Attorney, Agent, or Firm—Jacobson, Price, Holman & Stern

[57] ABSTRACT

A human stomach-shaped pouch is provided including a closed fundus and an open antrum as well as major and minor curvatures extending between the fundus and the antrum. The minor curvature includes an esophageal opening closely adjacent the fundus and the pouch includes a slot extending along the inner curvature and communicating the esophageal opening and the open antrum, the pouch being constructed of high performance silicone elastomer, 30 durometer, and including "DACRON" tricot knit (DuPont D116) imbedded in the margins of the pouch extending along the inner curvature slot. Also, an annular collar provided with a radial slit is provided also constructed of silicone elastomer and is secured to the outer surface of the pouch about the esophageal opening with the slot thereof registered with the slot of the pouch. The pouch is constructed with smooth inner and outer surfaces throughout and is provided with small openings formed therethrough at points spaced apart thereover.

9 Claims, 2 Drawing Sheets

FENESTRATED GASTRIC POUCH

BACKGROUND OF THE INVENTION

1. Field of the Invention

This invention relates to a slotted, preformed pouch for disposition and securement about the stomach of a human after inversion of the greater curvature of the stomach in order to appreciably reduce the internal volume thereof, the pouch being flexible and expandable to a limited degree, but operable to appreciably reduce the amount of food which may be contained within the stomach.

2. Description of Related Art

Various different forms of medical apparatuses including some of the general structural and operational features of the instant invention as well as internal organ supporting devices and structures for producing a multi-layered prosthesis heretofore have been provided such as those disclosed in U.S. Pat. Nos. 3,983,863, 4,271,828, 4,403,604, 4,497,074, 4,747,849, 4,770,664 and 4,854,316. However, these previously known structures do not include the overall combination of structural and operational features of the instant invention.

U.S. Pat. No. 4,403,604 is closest to the general structure and operation of the instant invention. However, this patent discloses a mesh gastric pouch which may not be easily removed from a patient's stomach inasmuch as the outer layers of the stomach tend to grow through and become permanently attached to the mesh of the pouch. Further, the mesh pouch of U.S. Pat. No. 4,403,604 includes considerable external stitching which may interfere with adjacent body tissue and requires considerably more time to install once the abdomen has been entered and maximum exposure of the stomach has been obtained.

SUMMARY OF THE INVENTION

In the past there have been several different surgical procedures which have been attempted to correct morbid obesity. These various attempts have included gastric bypasses, small-bowel bypasses and other radical procedures. While these procedures have proven more effective than psychiatric or dietary regimes in achieving substantial and lasting reduction for morbidly obese patients, they often have resulted in frequent and serious psychologic and metabolic derangements. For these reasons at least one study was begun to development a more physiologic operation that would reduce caloric intake without altering the continuity of the gastro intestinal tract. The objective at the outset of this study was reduce the reservoir capacity of the stomach and thereby achieve early satiety.

As a result of the aforementioned study, experiments were made on animals involving the inversion of the greater curvature of the stomach. Post operatively these animals could eat only small amounts without vomiting and all lost weight. However, within a relatively short period of time following surgery, they were observed to be eating progressively larger meals and soon regained normal weight. By tests then made on the animals it was revealed that their stomachs had regained their normal size and shape. Accordingly, a more lasting method of reducing the reservoir capacity of the stomach was needed. Such a more lasting method comprises the subject of the invention wherein the stomach is wrapped in a pouch which is preoperatively constructed of a predetermined size and which is then secured about the stomach.

The pouch disclosed in U.S. Pat. No. 4,403,604 has proven to be effective in achieving the desired end result, but, because of the structural nature of this previously known pouch, the time required for installation thereof is excessive. Further, it has been found that the outer layer of the stomach tissue will bind sufficiently t the mesh material of the pouch to make removal of the pouch difficult.

Accordingly, a need exists for an improved form of gastric pouch which may be more quickly installed during the operative procedure and which will be more readily removable and less irritating to adjacent tissues.

The gastric pouch of the instant invention is molded of high performance silicone elastomer to the precise desired size of the patient's stomach and is closed at the upper fundus, includes an esophageal opening and is open at the antrum, the minor curvature of the pouch including a full length slot from the esophageal opening to the open antrum end. In addition, an annular collar provided with a radial slit and constructed of high performance silicone elastomer is provided and secured to the outer surface of the pouch about the esophageal opening with the slit of the collar registered with the slot in the minor curvature of the pouch. Finally, those marginal portions of the pouch disposed on opposite sides of the minor curvature slot are reinforced through the utilization of "DACRON" (polyethylene terephtalate) and tricot knit material imbedded within the silicone elastomer of the pouch between the inner and outer surfaces thereof.

The main object of this invention is to provide a gastric pouch of a construction which will enable its economic manufacture in a form to be readily secured about the stomach in order to prevent expansion of the stomach beyond a predetermined size, after the major curvature of the stomach has been inverted. In this manner, the reserve capacity of the stomach is substantially reduced and early satiety results together with a substantial reduction of weight, in most cases.

Another object of this invention is to provide a stomach pouch which may be surgically applied for the intended purpose and by a procedure which is relatively free of postoperative complications.

A further object of this invention is to provide a stomach pouch which may be surgically applied for the intended purpose by a procedure which requires a minimum amount of time.

Still another object of this invention is to provide a gastric pouch in accordance with the preceding objects and constructed and applied in a manner such that subsequent removal of the pouch may be effected more readily than with a mesh pouch.

A final object of this invention to be specifically enumerated herein is to provide a gastric pouch in accordance with the preceding objects and which may be inexpensively produced, utilized to perform the intended procedure with a minimum of risk and which will be effective in achieving substantial reduction of morbid obesity, in most cases.

These together with other objects and advantages which will become subsequently apparent reside in the details of construction and operation as more fully hereinafter described and claimed, reference being had to the accompanying drawings forming a part hereof, wherein like numerals refer to like parts throughout.

DETAILED DESCRIPTION OF THE INVENTION

Figure 1:
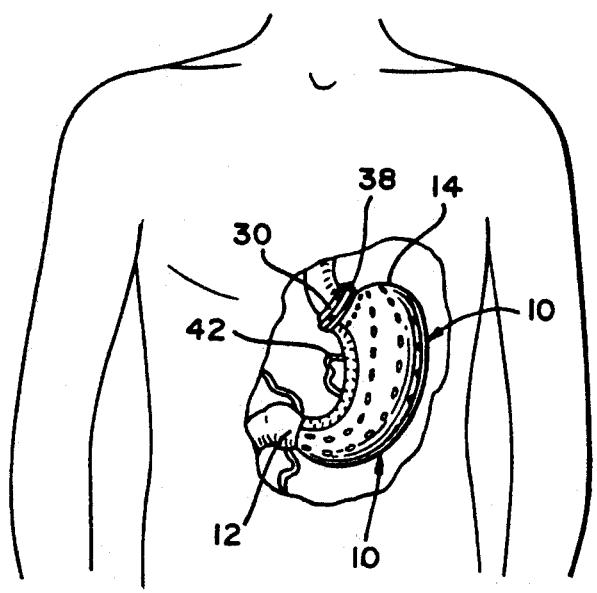
FIG. 1 is a perspective view illustrating the gastric pouch as applied to the stomach of a patient.
Figure 2:
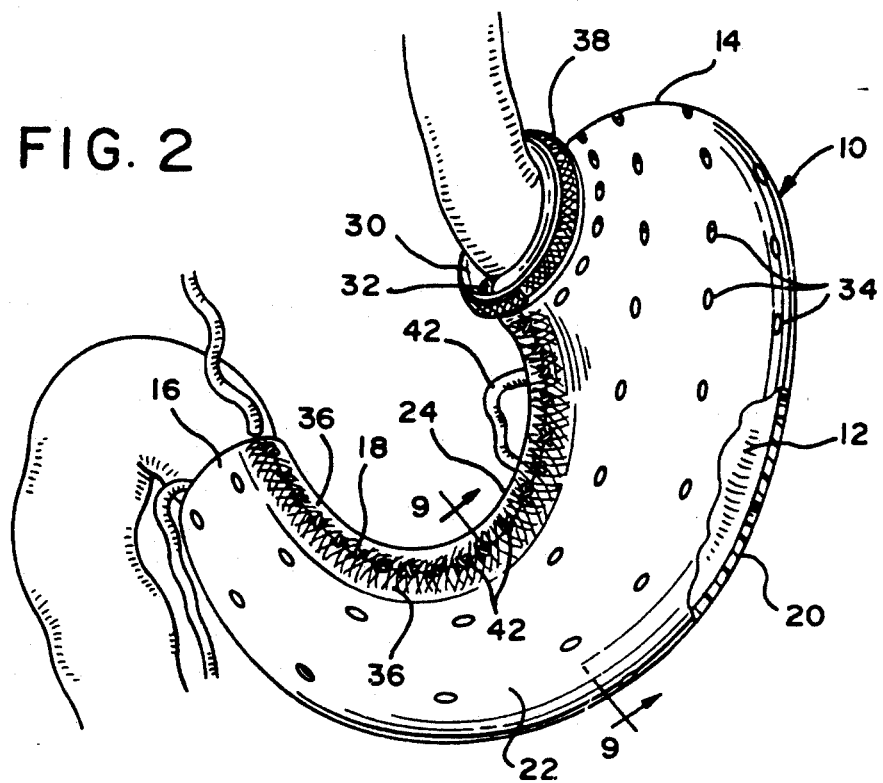
FIG. 2 is an enlarged perspective view of the pouch as applied to the stomach of a patient and with portions of the major curvature of the pouch being broken away and illustrated in section.
Figure 4:
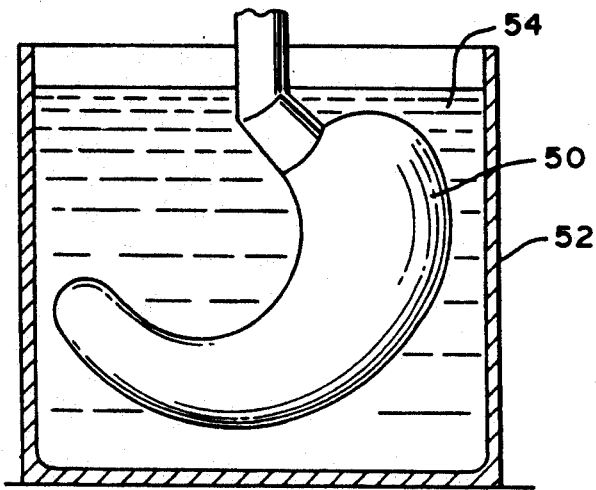
FIG. 4 is schematic view illustrating the manner in which the initial thickness of the pouch may be formed on a mandrel.
Figure 5:
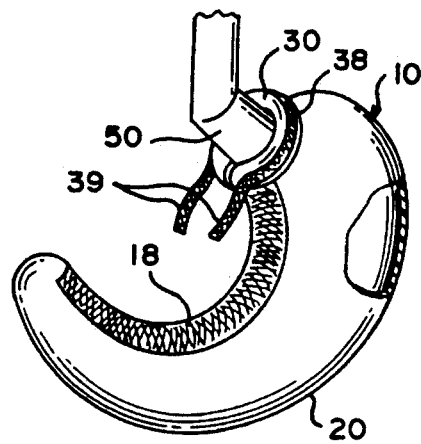
FIG. 5 is a perspective view of the pouch in a partially completed state.
Figure 6:
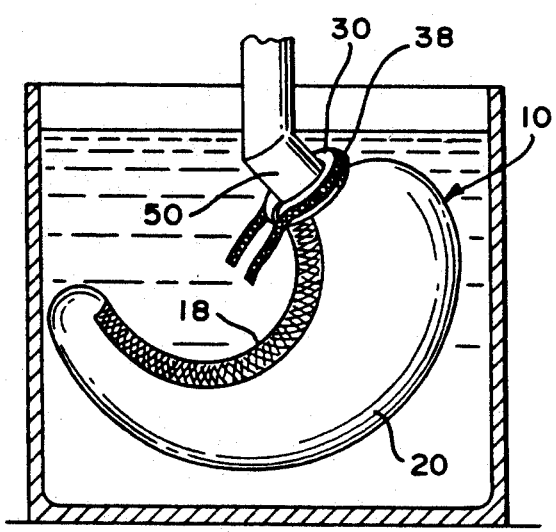
FIG. 6 is a schematic view illustrating the final dipping step of production of the pouch.
Figure 8:
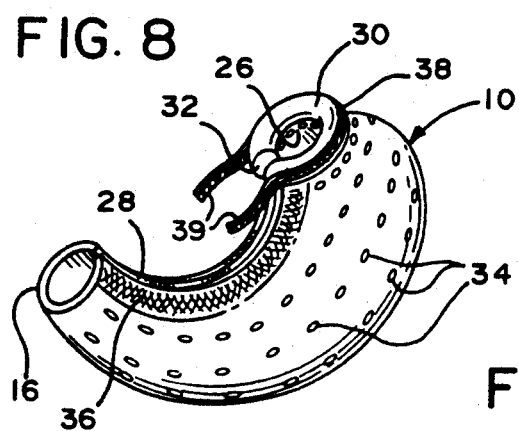
FIG. 8 is a perspective view of the completed pouch.
Figure 9:
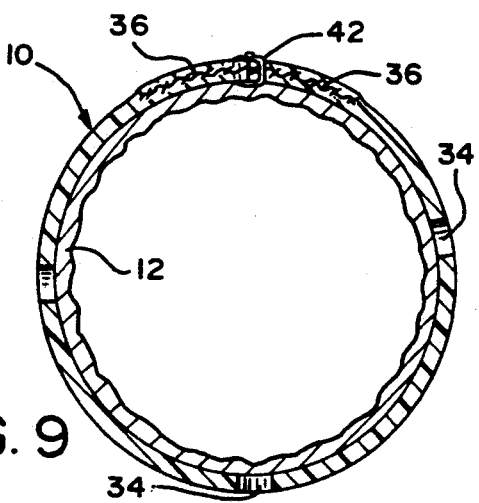
FIG. 9 is an enlarged fragmentary sectional view taken substantially upon the plane indicated by the section line 9—9 FIG. 2.

Referring now more specifically to the drawings, the numeral 10 generally designates the gastric pouch of the instant invention and the pouch 10 is illustrated in FIG. 8 in its configuration immediately prior to application to a stomach and in FIGS. 1 and 2 as fully applied to a stomach 12.

The pouch 10 is constructed of medical grade, high performance silicone elastomer, 30 durometer, and imbedded "DACRON" (polyethylene terephtalate) tricot knit (DuPont D116) used to reinforce the tabs on the esophageal ring, the suture edges of the gastric pouch opening and the area of the pouch to be custom cut by the surgeon for each patient for the epigastric artery.

The purpose of the imbedded "DACRON" polyethylene terephtalate knit is to provide suture retention and additional tear resistance in these areas. Both materials have a long history of use for construction of implants. The silicone elastomer is the same material used for the past eight to ten years as the outer envelope end "SILASTIC" (medical grade silicone rubber) brand memory implant prosthesis. It is also used in tissue expanders. The "DACRON" polyethylene terephtalate knit has been used for more than two decades in reinforce "SILASTIC" brand sheeting and in a variety of other implants including mammary implant prosthesis and tissue expanders.

The pouch 10 includes a fundus 14 which is closed and an antrum 16 which is open. In addition, the pouch 10 includes a minor curvature side 18, a major curvature side 20, an anterior side 22 and a posterior side 24, the sides 18, 20, 22 and 24 extending the full length of the curved pouch from the fundus 14 to the antrum 16. Further, the pouch 10 includes smooth inner and outer surface throughout and an esophageal opening 26 closely adjacent the fundus on the inner curvature side 18 and the inner curvature side 18 includes a longitudinal slot 28 extending from the opening 26 to the open antrum end 16.

A radially split annular collar 30 is secured to the outer surfaces of the pouch 10 disposed about the opening 26 with the slit 32 of the collar 30 registered with the slot 28 of the pouch 10. The pouch 10 and collar 30 are constructed of medical grade silicone elastomer and the pouch 10 is provided with a plurality of holes 34 spaced thereover which are generally 3 mm in diameter and spaced apart generally between 1½ and 2 cm.

Also, the marginal portions of the pouch 10 disposed on opposite sides of the slot 28 are reinforced with "DACRON" (polyethylene terephtalate) tricot knit (DuPont D116) strips 36. In addition, the collar 30 has a further strip 38 corresponding to the strips 36, but slightly narrower, secured thereto and includes free ends 39 disposed on either side of the slit 32. The operational procedure involving the application of the pouch 10 about a patient's stomach is carried out in substantially the same manner as that set forth in U.S. Pat. No. 4,403,604, except that it is pointed out that the pouch 10 is cut as at 40, (see FIG. 3) in order to provide an opening for the left gastric artery 42 in the posterior wall or side 24 of the pouch 10. In addition, the free ends 39 of the strip 38 are sutured together as required about the esophagus to prevent herniation of the stomach and the slot 28 is closed by suitable sutures 42.

In constructing the pouch 10, a mandrel is provided of the desired shape and a tank 52 is also provided containing a solvent dispersion 54 of silicone elastomer typically containing 13 percent by Weight silicone elastomer, the solvent comprising methylochloroform (1, 1, 1, trichloroethane).

Figure 7:
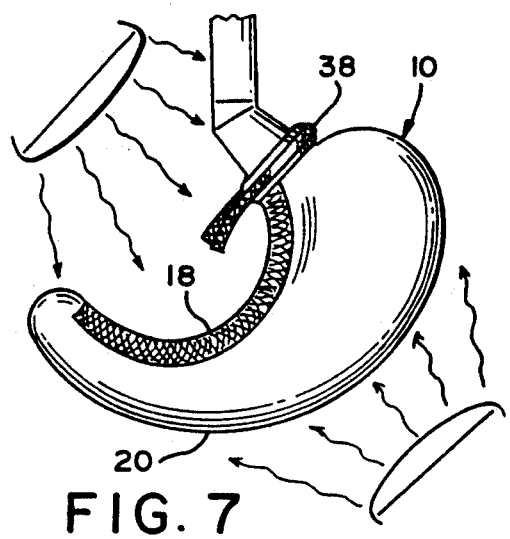
FIG. 7 is a schematic view of the pouch illustrating the manner in which the latter is heated between successive dipping steps in order to cure the silicone elastomer as well as to "vulcanize" the esophageal ring to the body of the pouch.

The mandrel 50 is dipped repeatedly until an adequately thick layer of elastomer has been deposited on the metal mandrel. The mandrel is dried in air between dips and after the last dip to remove solvent. It is then placed in an oven at room temperature and the oven is gradually heated to 280° F. degrees and maintained at that temperature for one hour, the heating process being schematically illustrated in FIG. 7 upon a completed pouch.

The silicone elastomer layer on the mandrel 50 at this point is between point 0.020 and 0.025 inches. Thereafter, unvulcanized "DACRON"-reinforced HP-100 medical grade silicone elastomer sheeting is prepared by calendaring a 0.010 inch layer of elastomer on both sides of "DACRON" (polyethylene terephtalate) knit D116 pressed between two layers of polyethylene film to permit its handling. This reinforced sheeting is then cut to shape, one layer of the plastic film is removed and the unvulcanized sheeting is applied to the cured silicone elastomer on the mandrel in the appropriate areas to reinforce the suture opening or slot 28 and the area to be cut during surgery for the left gastric artery. Thereafter, the second layer of polyethylene film is removed and the mandrel is again placed in a oven at room temperature and the temperature is gradually increased to 280° F. degrees and maintained for approximately one hour to cure the sheeting. The mandrel 50 is again dipped repeatedly until an adequately thick layer of elastomer has been deposited over the first layer.

The mandrel is then cooled to room temperature, the pouch is cut from around the neck of the mandrel, the antrum end is cut off and the slot 28 is formed so that it can be latter applied around the stomach 12 and the slot 28 in the pouch 10 closed with sutures to secure it in place.

The esophageal ring or collar 30 is molded from HP-100 medical grade silicone elastomer, 30 durometer, by conventional transfer molding procedures. Flash is removed from the parting line and the strip 38, cut from the previously described reinforced, unvulcanized HP-100 medical grade silicone elastomer sheeting, is pressed to the outside of the esophageal ring or collar 30 after collar 30 has been applied to the outer surface of the pouch 10 about the opening 26. Then, the pouch is again placed in a room temperature oven, warmed to 280° F. degrees and cured at that temperature for one hour. By this process, the strip 38 is secured to the collar 30 and the collar 30 is secured to the pouch 10 about the opening 26. The pouch 10 is then cooled and reinstalled on the mandrel. Thereafter, a reference model pouch with holes formed therein is put over the freshly made pouch and the freshly made pouch on the mandrel is marked through the holes in the model pouch. The freshly made pouch is then removed from the mandrel and the holes 34 are made with punch.

The pouch 10 is then washed first with water and then is with isopropyl alcohol to remove any marking remaining on the pouch.

It is to be noted that the "DACRON" (polyethylene terephtalate) knit applied along the lesser curvature side 18 of the pouch 10 is cut into two strips of reinforcing material when the slot 28 is formed. Also, it will be noted that strip 38 is not bonded to those portions of the collar 30 immediately adjacent the slit 32. Rather, the free ends 39 of the strip 38 (suture tab sections) are not anchored directly to those portions of the collar 30 adjacent the slot 32, inasmuch as it may be necessary to variably overlap and secure together the strip ends in order to custom fit the collar 30 about the patient's esophagus.

Figure 3:
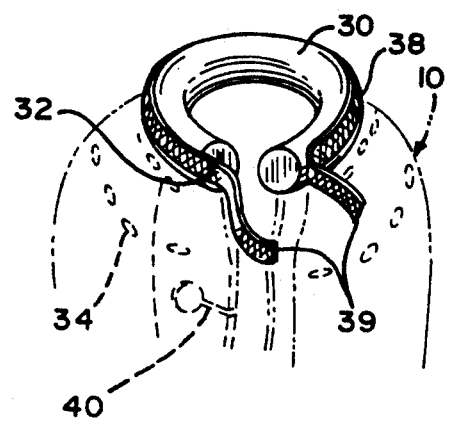
FIG. 3 is an enlarged perspective view of the esophageal collar of the pouch with the latter fragmentarily illustrated in phantom lines.

Of course, as the pouch 10 is initially placed about the stomach 12, the left gastric artery 42 is received in the opening 40, see FIG. 3.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new as follows:

1. A hollow, flexible and thin-walled gastric pouch of human stomach-shaped configuration including smooth inner and outer surfaces throughout and constructed of an inert elastomeric material, said pouch including an upper fundus end, remote greater curvature and lesser curvature sides extending from said fundus end to an open antrum end remote from said fundus end and posterior and anterior sides also extending between said ends and said greater and lesser curvature sides, said fundus end including an esophageal opening and further including an elongated slot having margins, said slot being formed along said lesser curvature side, extending longitudinally from said opening to said open antrum end, only the margins extending along opposite sides of said slot being reinforced with reinforcing material, with the remainder of said pouch being free of internal reinforcement, said reinforcing material comprising a reinforcing mesh imbedded fully within said material between said inner and outer surfaces of said pouch, said mesh serving as reinforcing for suturing when securing said pouch about a patient's stomach.

2. The pouch of claim 1 including an annular collar of inert, flexible material having a generally radial slit with two opposing ends, said collar being bonded to the outer surface of said pouch about said esophageal opening with said slit registered with said slot, said two opposing ends having corresponding elongated, flexible mesh reinforced suture tab sections secured to the outer surfaces thereof, said tab section including free ends extending beyond the opposing ends.

3. The pouch of claim 1 wherein said pouch has openings formed therethrough spaced generally equally over the surface of said pouch, said openings being generally 3 mm in diameter and spaced apart generally 2.0 cm to 3 cm.

4. The pouch of claim 3 wherein said inert elastomeric material comprises a high performance medical grade silicone.

5. The pouch of claim 2 wherein said reinforcing mesh comprises a polyethylene terephtalate tricot knit.

6. The pouch of claim 2 wherein said collar is constructed of high performance medical grade silicone elastomer.

7. The pouch of claim 6 wherein said pouch has openings formed therethrough spaced generally equally over the surface of said pouch, said openings being generally 3 mm in diameter and spaced apart generally 2.0 cm to 3 cm.

8. The pouch of claim 7 wherein said inert elastomeric material comprises a high performance medical grade silicone.

9. The pouch of claim 2 wherein said suture tab sections are free of bonding to said annular collar closely adjacent said radial slit.

* * * * *